US007434540B2

(12) United States Patent
Aylen et al.

(10) Patent No.: US 7,434,540 B2
(45) Date of Patent: Oct. 14, 2008

(54) ANTIMICROBIAL ADDITIVE FOR LARGE ANIMAL OR POULTRY BEDDINGS

(75) Inventors: Peter Aylen, Kamloops (CA); Steve Gurney, Kamloops (CA); Dean Clark, Kamloops (CA)

(73) Assignee: Absorbent Products Ltd., British Columbia (CA)

( * ) Notice: Subject to any disclaimer, the term of this patent is extended or adjusted under 35 U.S.C. 154(b) by 187 days.

(21) Appl. No.: 10/967,112

(22) Filed: Oct. 14, 2004

(65) Prior Publication Data

US 2006/0081194 A1 Apr. 20, 2006

(51) Int. Cl.
*A01K 29/00* (2006.01)
*A61L 2/00* (2006.01)
(52) U.S. Cl. ..................... 119/173; 424/76.6
(58) Field of Classification Search ............... 119/173, 119/171, 172, 28.5, 442, 447, 479, 651; 424/76.6
See application file for complete search history.

(56) References Cited

U.S. PATENT DOCUMENTS

| | | | | |
|---|---|---|---|---|
| 2,708,418 | A * | 5/1955 | Sugarman et al. | 119/172 |
| 3,916,831 | A * | 11/1975 | Fisher | 119/173 |
| 3,921,581 | A * | 11/1975 | Brewer | 119/173 |
| 4,306,516 | A * | 12/1981 | Currey | 119/171 |
| 4,641,605 | A * | 2/1987 | Gordon | 119/173 |
| 4,881,490 | A * | 11/1989 | Ducharme et al. | 119/173 |
| 5,109,805 | A | 5/1992 | Baldry et al. | |
| 5,448,967 | A * | 9/1995 | Ryan | 119/171 |
| 5,960,743 | A * | 10/1999 | Taylor | 119/173 |
| 6,039,004 | A * | 3/2000 | Goss et al. | 119/172 |
| 6,196,156 | B1 * | 3/2001 | Denesuk et al. | 119/28.5 |
| 6,287,550 | B1 * | 9/2001 | Trinh et al. | 424/76.6 |
| 6,303,111 | B1 * | 10/2001 | Maurer et al. | 424/76.1 |
| 6,435,135 | B1 * | 8/2002 | Johnston et al. | 119/171 |
| 6,436,384 | B2 * | 8/2002 | Santoiemmo | 424/76.6 |
| 6,543,385 | B2 * | 4/2003 | Raymond et al. | 119/171 |
| 6,622,658 | B2 * | 9/2003 | McPherson et al. | 119/171 |
| 6,854,421 | B2 * | 2/2005 | Opfel | 119/173 |
| 6,991,783 | B2 * | 1/2006 | Santoiemmo | 424/76.6 |
| 2001/0027755 | A1 * | 10/2001 | Denesuk et al. | 119/709 |
| 2002/0176839 | A1 * | 11/2002 | Santoiemmo | 424/76.6 |
| 2003/0133993 | A1 * | 7/2003 | Hutcheson et al. | 424/647 |
| 2003/0192485 | A1 * | 10/2003 | Opfel | 119/526 |
| 2003/0205205 | A1 * | 11/2003 | Opfel | 119/526 |
| 2003/0209203 | A1 * | 11/2003 | Opfel | 119/173 |
| 2004/0069237 | A1 * | 4/2004 | McPherson et al. | 119/171 |
| 2006/0005784 | A1 * | 1/2006 | Lind | 119/651 |

OTHER PUBLICATIONS

Absorbent Products Ltd, Stall Dry (tm) and Stall Dry (tm) Equine Bedding product literature.*
Material Safety Data Sheet, Stall Dry (tm) Plus Deodorizer with Antimicrobial.*
Stall Dry (tm) Trademark Search.*
Material Safety Data Sheet, Stall Dry (tm) Deodorizer.*

* cited by examiner

*Primary Examiner*—Yvonne R. Abbott
(74) *Attorney, Agent, or Firm*—Amster, Rothstein & Ebenstein LLP

(57) ABSTRACT

The present invention provides a method for reducing ammonia levels, odor, microorganisms and insects in large animal stalls using a bedding material additive comprising a clay-based particulate absorbent material and an aliphatic bromo-nitro-bactericide.

31 Claims, 6 Drawing Sheets

Mean Ammonia Levels (ppm) Measured 30 cm Above Manure

Figure 1. Mean Ammonia Levels (ppm) Measured 30 cm Above Manure

Figure 2. Percent Difference in Ammonia Levels Between Untreated and BARN FRESH PLUS-Treated Section

*Figure 3*  Mean (± SE) of Pooled (0-14 days) Ammonia Levels (PPM) Under Pine Wood Shavings in Horse Stalls treated with Antibacterial Stall Dry (NewSD), Original Stall Dry (OldSD) and Untreated Controls Before Rotation of Treatments

*Figure 4* Mean (± SE) of Pooled (0-7 and 14 days) Ammonia Levels (PPM) on Urine Soaked Wooden Floors in Horse Stalls treated with Antibacterial Stall Dry (NewSD), Original Stall Dry (OldSD) and Untreated Controls after Rotation of Treatments

*Figure 5*   Mean (± SE) of Ammonia Levels (PPM) on Urine Soaked Wooden Floors in Horse Stalls Two Days after Treatment with Antibacterial Stall Dry (NewSD), Original Stall Dry (OldSD) and Untreated Controls after Rotation of Treatments Mean (± SE) of Ammonia Levels (PPM) on Urine Soaked Wooden Floors in Horse Stalls 14 Days after Treatment with Antibacterial Stall Dry (NewSD), Original Stall Dry (OldSD) and Untreated Controls after Rotation of Treatments

ANTIMICROBIAL ADDITIVE FOR LARGE ANIMAL OR POULTRY BEDDINGS

FIELD OF THE INVENTION

The present invention pertains to the field of bedding materials for use in large animal stalls and poultry barns.

BACKGROUND OF THE INVENTION

The respiratory systems of horses, cattle, hogs and poultry can be harmed by the presence of ammonia in their barns, stalls, pens and other enclosures. At high enough levels, the damage can adversely affect weight gain and feed conversion [Carr and Nicolson, 1980: "Broiler Response to three Ventilation rates, Am Soc. Arg. Eng 2:414-418]. It is therefore desirable to reduce the quantity of ammonia to which these animals are exposed.

Ammonia is formed by enzymatic hydrolysis of urea, which is present in animal waste. The hydrolysis is catalyzed by the enzyme urease, which is produced by certain microorganisms that are commonly found in animal waste. Inhibition of microbial growth through the addition of an antimicrobial agent to animal waste should therefore reduce ammonia production.

Inhibiting microbial growth is also desirable because certain microbes can directly harm animals. For example, *Staphylococcus, Streptococcus* and *Escherichia coli* bacteria cause mastitis, a disease of the mammary tissue of dairy cows. Other bacteria have been known to increase the mortality rates of poultry and reduce weight gain in other animals.

The concept of using a particulate absorbent material comprising an antimicrobial agent such as Bronopol™ is taught in the art (see Baldry et. al U.S. Pat. No. 5,109,805). The product disclosed in Baldry et al. is a small animal litter for household pets, particularly cats.

As a household pet litter, clay based absorbent materials are typically used in un-admixed form and in sufficient quantity to effectively absorb the entire volume of the pet urine into the particulate material to maintain dry conditions in the litter box. For this purpose, clay-based materials, which have good absorbency characteristics, are commonly used. In such applications, all or substantially all of the absorbed urine is brought into intimate contact with the antibacterial agent carried in or on the particulate absorbent material thereby establishing conditions favourable to significant reductions in bacterial growth in litter applications disclosed in Baldry et al.

However, large animal stall and poultry barn bedding applications are subject to vastly different conditions than those of domestic pet litter applications. In order to cope with the very large volumes of urine produced by large animals such as horses and cows, or large numbers of animals, such as poultry or hogs, absorbent stall bedding materials must be applied to the stall floor in large quantities and changed frequently. In view of cost considerations, a clay-based absorbent material such as the domestic litter disclosed in Baldry et al. is excluded as a suitable large animal stall bedding material. Instead, the bedding materials of choice for large animal stalls and poultry barns are wood shavings and/or saw dust and/or straw, which are commonly available at a relatively low price.

While Baldry et al. discloses that antibacterial agents can be incorporated into or surface treated onto a variety of other absorbent particulate materials, the cost of treating wood shavings or straw with a bactericidal agent in the manner disclosed in Baldry et al. would be prohibitive and effectively excludes such an application of the teachings of Baldry et al. to large animal stall applications.

As noted in Baldry et al. at column 2, line 64 to column 3, line 7, the presence and nature of the absorbent material exercises a considerable effect on bactericidal action, and a given bactericidal agent may be more or less effective against bacteria in urine alone or depending on the particular absorbent material of which the litter is composed. Thus, the effectiveness of anti-bacterial agents in small animal litter applications such as those disclosed in Baldry et al. is not a reliable indicator of their effectiveness in the radically different large animal stall applications, or in instances such as poultry barns where larger areas require treatments.

Therefore a need remains for a cost-effective method of employing the antimicrobial properties of known bactericidal materials to large animal stall applications.

SUMMARY OF THE INVENTION

In accordance with one aspect of the invention there is provided a method of reducing ammonia levels in a large animal stall or poultry barn comprising the step of applying an additive comprising a clay-based particulate, wherein said particulate contains an antimicrobial agent, over the floor of an animal stall or barn in an amount of between 0.22 kg/m$^2$ and 0.43 kg/m$^2$.

DETAILED DESCRIPTION OF THE INVENTION

Figure 1:
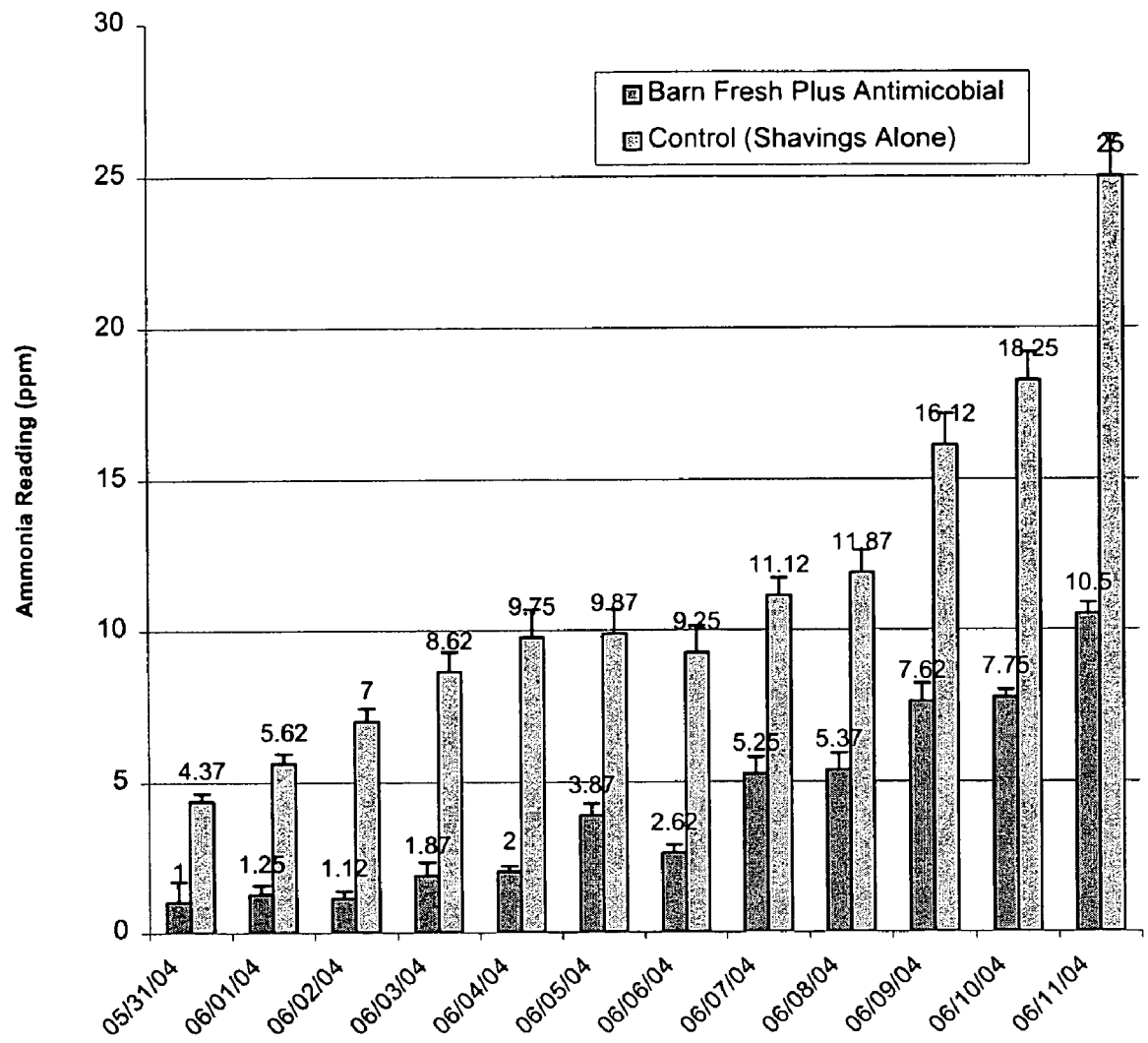
FIG. 1 is a graph showing the mean ammonia levels (ppm) measured 30 cm above the manure over the test period using a clay-based particulate material with an antimicrobial agent ("Barn Fresh Plus") and without any treated material, (control) shavings alone.

The method of the present invention reduces ammonia levels in a large animal stall or poultry barn and comprises the steps of the applying a minor amount of a clay-based particulate material comprising a antimicrobial agent and a major amount of an absorbent bedding material over the floor of an animal stall or barn. It has surprisingly been found that a clay-based particulate which contains an antimicrobial agent can be used in relatively small amounts in combination with inexpensive bedding materials such as wood shavings, saw dust or straw, which are commonly used in large animal stalls or poultry barns, to reduce microbial growth and thus decrease ammonia production caused by micro organisms associated with animal waste.

The clay-based particulate can comprise any of a number of suitable clay minerals including smectite, attapulgite, sepiolite, bentonite, kaolinite, gypsum, and zeolite. Preferably, the clay mineral is montmorrillonite.

Most preferably, the clay material is a naturally occurring mixture of montmorrillonite clay and diatomaceous earth such as is available from Western Industrial Clay Products under the trade names Barn Fresh™ and Stall Dry™. Not only does the montmorrillonite clay have exceptional absorbency characteristics which makes it suitable for absorbing urine that has passed through the straw, saw dust or wood shaving bedding materials, the diatomaceous earth component is effective as an insecticidal agent to reduce the number insects or insect larvae in the stall or barn.

Preferably, the antimicrobial agent is 1,3-Propanediol, 2-bromo, 2-nitro, which is sold in powder form under the trade name Bronopol™ and in liquid form under the trade name Myacide™ and is present in the clay-based particulate in a concentration of from 50 to 250 ppm. The antimicrobial agent can be combined into the clay-based particulate in the manner described in Baldry et al. In particular, the antimicrobial agent may be admixed with the clay material during the particle forming process. In the alternative, particles of the clay based-particulate are treated with the antimicrobial agent, by means of the clay travelling through a gravity fed 6" diameter pipe at a flow rate of approximately 3.5 tonnes per hour. The clay material passes through a misting spray of antimicrobial agent at a pre-determined, pre-mixed concentration. In an alternative method of application, a known amount of clay travelling on a moving conveyor belt is sprayed with Myacide™ at an application rate pre-determined to achieve 250 ppm, or other desired concentrations.

In addition to the use of Bronopol™ or Myacide™ as the antimicrobial agent, an ammonia reducing agent such as phosphoric acid, citric acid, acetic acid or aluminium sulphate and a urease inhibitor such as cyclohexylphosphoric triamide, phenyl phosporodiamidate, or n- (n-butyl) thiophosporic triamide can also be incorporated into or surface treated onto the clay-based particulate to further reduce the level of ammonia production.

In accordance with one aspect of the present invention, the clay-based particulate comprising the antimicrobial agent is first applied over the stall or barn floor, preferably in an amount of between 0.22 kg/m$^2$ and 0.43 kg/m$^2$. Thereafter, a layer of straw and/or wood shavings and/or sawdust in an amount and manner as is conventionally used in stall or barn applications is applied over the clay-based particulate. When used in this manner, the inexpensive straw and/or wood shavings and/or saw dust bedding material is used as the primary absorbent material, thereby permitting a relatively small quantity of the more expensive clay-based particulate to be used. By applying the clay-based particulate first, is remains in direct contact with the floor of the barn or stall where pools of urine tend to collect.

In accordance with another aspect of the invention, the clay-based particulate comprising the antimicrobial agent can be applied to the stall or barn floor, preferably in an amount of between 0.22 kg/m$^2$ and 0.43 kg/m$^2$, after a primary absorbent bedding material such as wood shavings, saw dust or straw has been applied. An advantage of this embodiment is that the additive can be applied without first clearing the floor of bedding material. It helps to dry the bedding material, thereby increasing its usage time and reducing bedding costs.

In accordance with yet another aspect of the invention, a minor amount of the clay based particulate comprising the antimicrobial agent can be admixed with a major amount of the absorbent bedding material such as wood shaving, saw dust or straw, preferably in a weight ratio of from 25:1000 to 75:1000, prior to application to the stall or barn floor. An advantage to this specific embodiment is that the application of clay particulate and absorbent bedding material can be accomplished in a single step. Furthermore, mixing in this manner tends to avoid the need of multiple applications of materials, particularly in poultry barns where 2 applications (one for bedding and one for clay particulate) would increase the operational costs.

EXAMPLES

Example 1

Ammonia Emissions from Poultry Manure

The study was undertaken in a standard high rise caged layer-facility that housed approximately 36,000 birds that were 19 weeks old and had been housed in the barn for 7 days at the beginning of the study. Manure was about 1 cm deep over a pine wood shavings base. The manure area was comprised of four pits (rows) each measuring 1.2 m×90.9 m. The rectangular-shaped barn was oriented in a north-south direction with air circulating fans on the east side and pit fans on the west side of the pit area.

A naturally occurring binary mineral particulate of about 50% diatomaceous earth and about 50% montmorrillonite clay into which had been incorporated commercially available Bronopol™ to yield a concentration of about 50 ppm was applied at a rate of 0.27 kg/m$^2$ over an area covering approximately 44% of the manure on all four pits for a distance of 40 m from the south wall of the barn. This comprised the treated section of the manure. The untreated section of the manure covered a distance of 40 m from the north wall of the barn. A buffer section of approximately 10 m was maintained between the treated and untreated sections.

Ammonia was measured at sixteen different locations in the treated and untreated sections immediately after application of the additive and once daily for the 11 day duration of the study. The measuring locations were located on the first and third rows from the east wall of the barn.

A Passport™ Five Star Person Alarm (Mine Safety Appliances Company, Pittsburgh, Pa. U.S.A.) was used to measure ammonia levels. The device was held approximately 20 cm above the centre of the manure pit during measurements.

Statistical comparisons between the treated and untreated sections were analysed using the Student's t-test method. The t test employs the statistic (t), with n−1 degrees of freedom, to test a given statistical hypothesis about a population parameter. The method is suitable for use with small sample sizes (<30) and when population standard deviation is unknown.

Results

Figure 2:
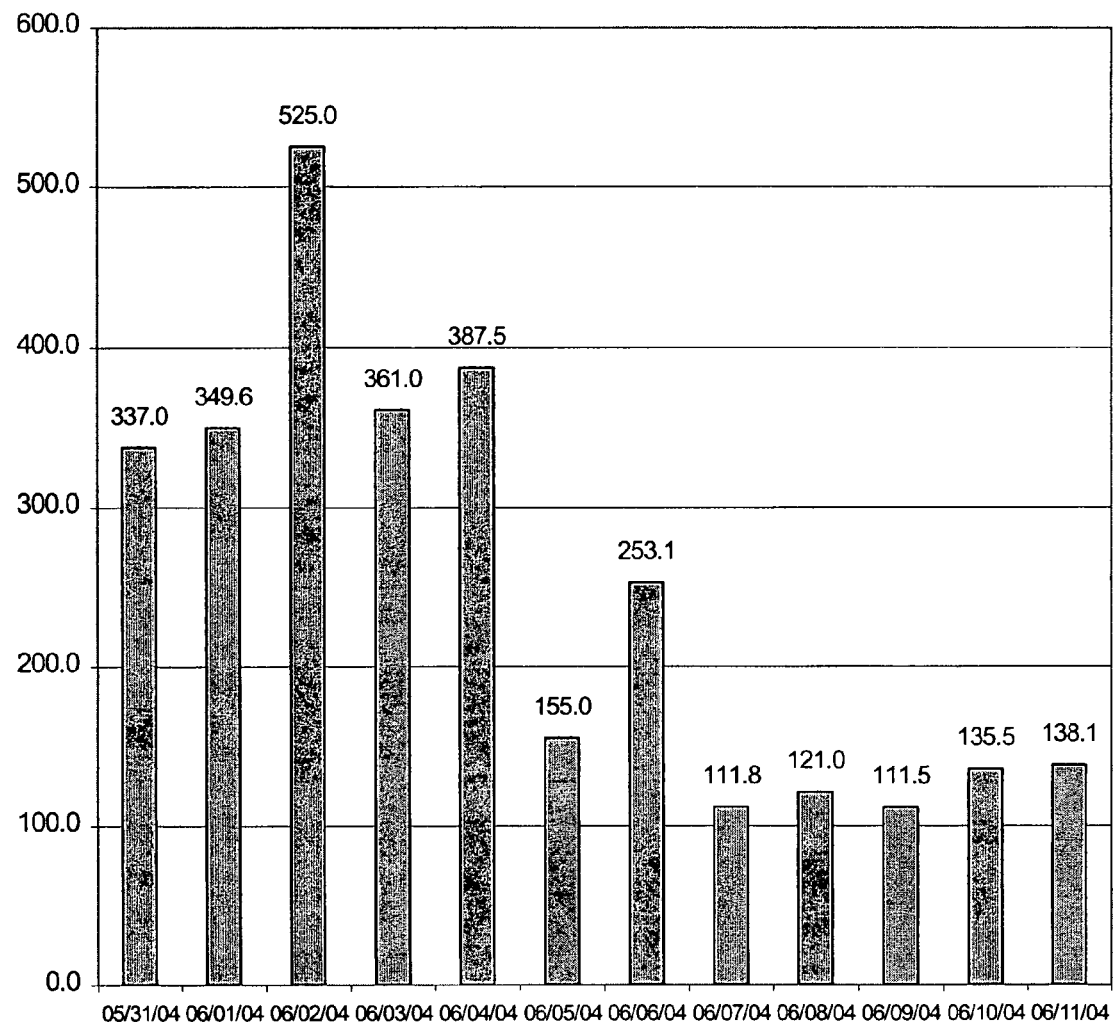
FIG. 2 is a graph showing the percent difference in ammonia levels between untreated sections and sections treated with a clay-based particulate material with an antimicrobial agent ("Barn Fresh Plus").
Figure 3:
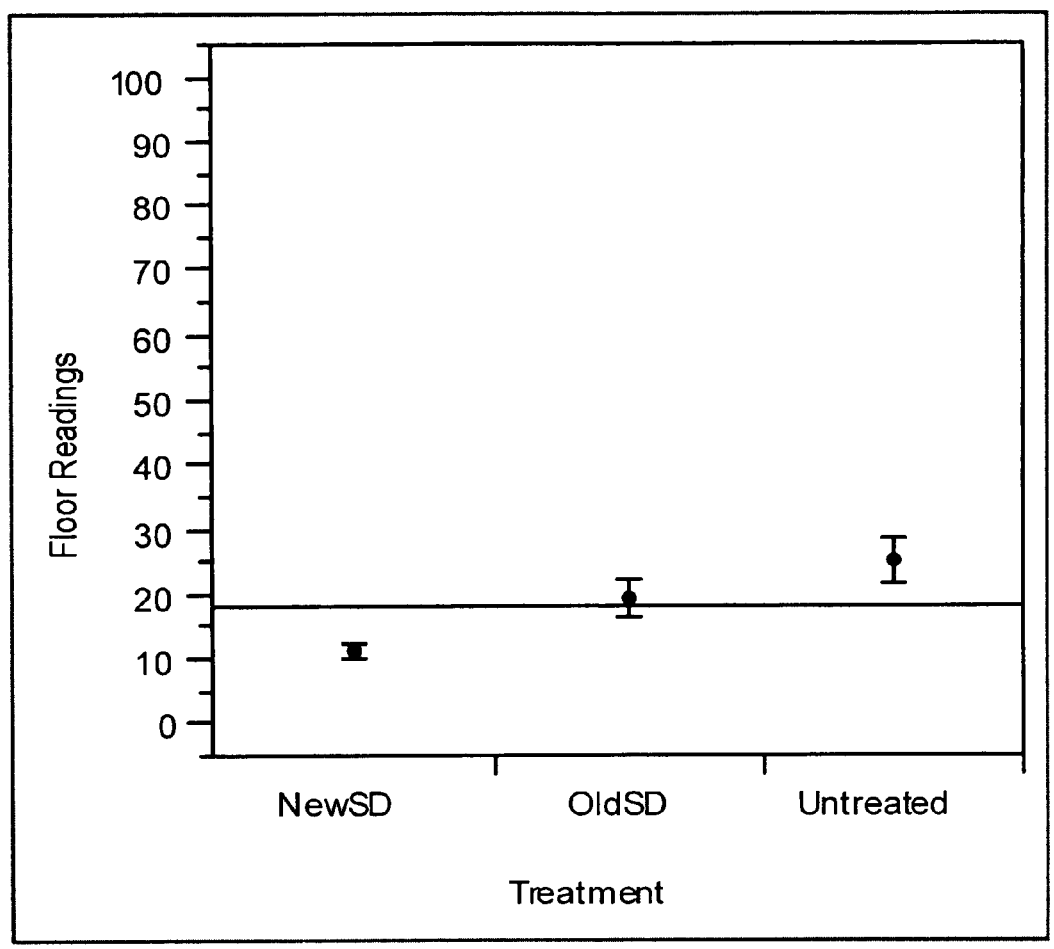
FIG. 3 is a graph showing mean (±SE) of pooled (0-14 days) ammonia levels (ppm) under pine wood shavings in horse stalls treated with a clay-based particulate material with an antimicrobial agent ("NewSD"), a clay-based particulate material without an antimicrobial agent ("OldSD") and untreated controls before rotation of treatments.
Figure 4:
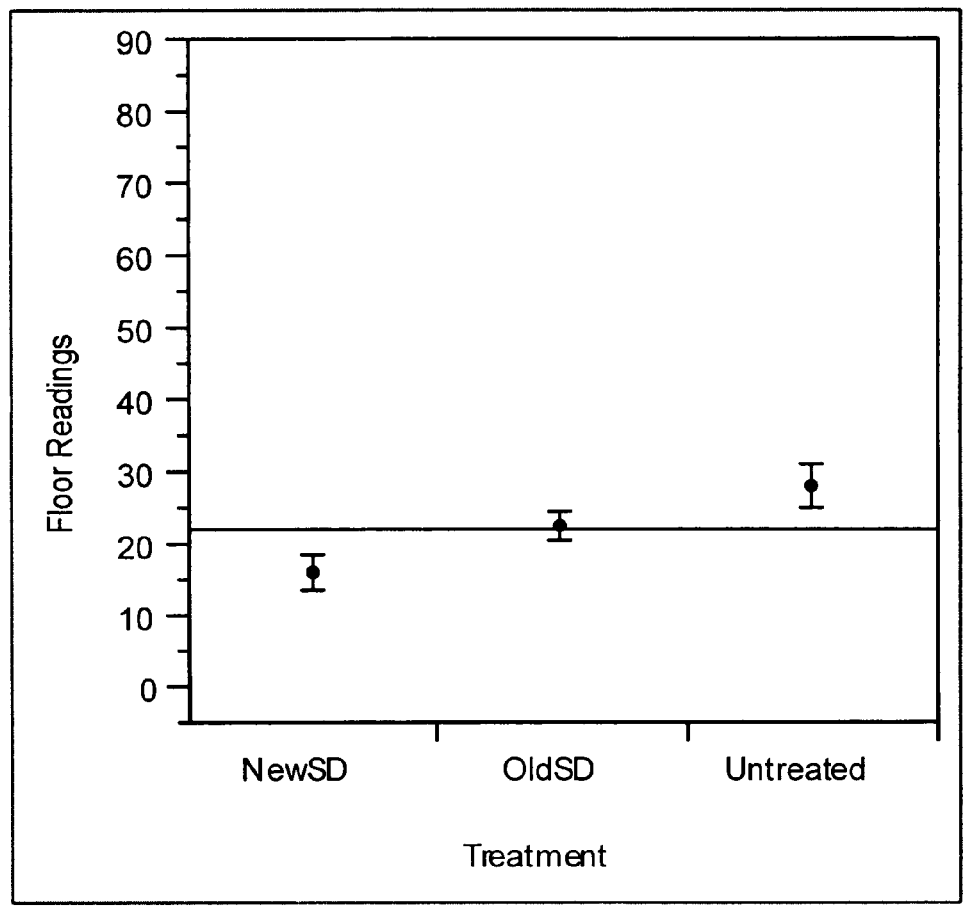
FIG. 4 is a graph showing mean (±SE) of pooled (0-7 and 14 days) ammonia levels (ppm) on urine soaked wooden floors in horse stalls treated with a clay-based particulate material with an antimicrobial agent ("NewSD"), a clay-based particulate material without an antimicrobial agent ("OldSD") and untreated controls after rotation of treatments.
Figure 5:
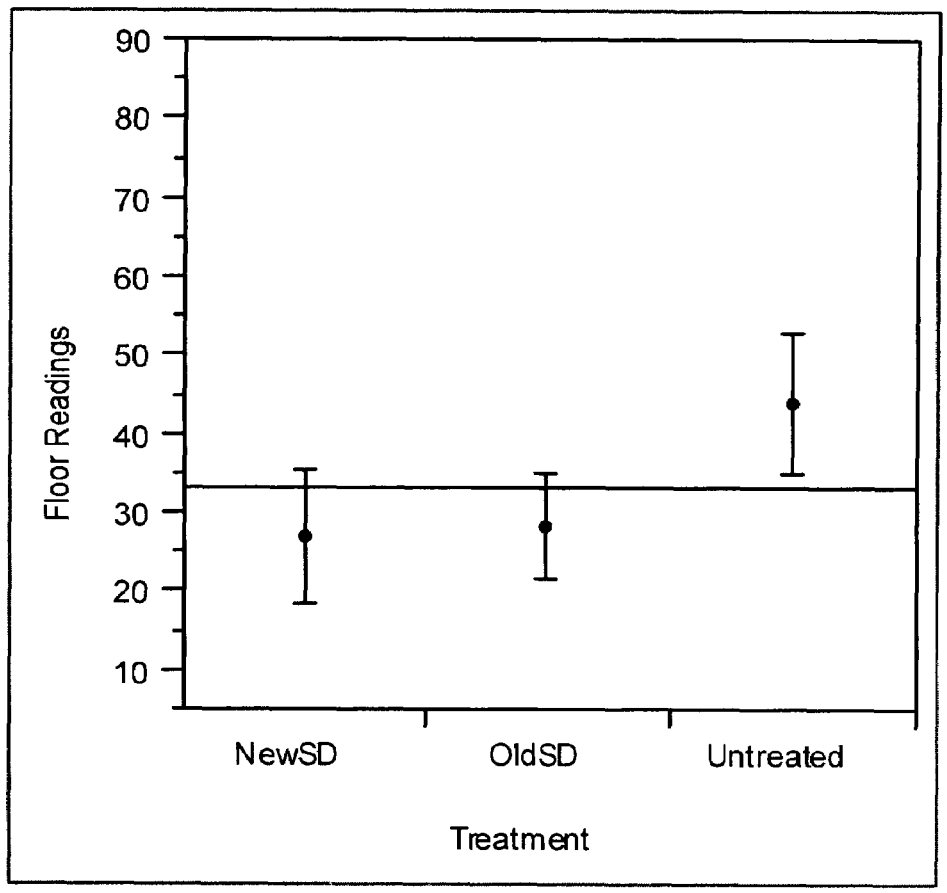
FIG. 5 is a graph of mean (±SE) of ammonia levels (ppm) on urine soaked wooden floors in horse stalls two days after treatment with a clay-based particulate material with an antimicrobial agent ("NewSD"), a clay-based particulate material without an antimicrobial agent ("OldSD") and untreated controls after rotation of treatments.
Figure 6:
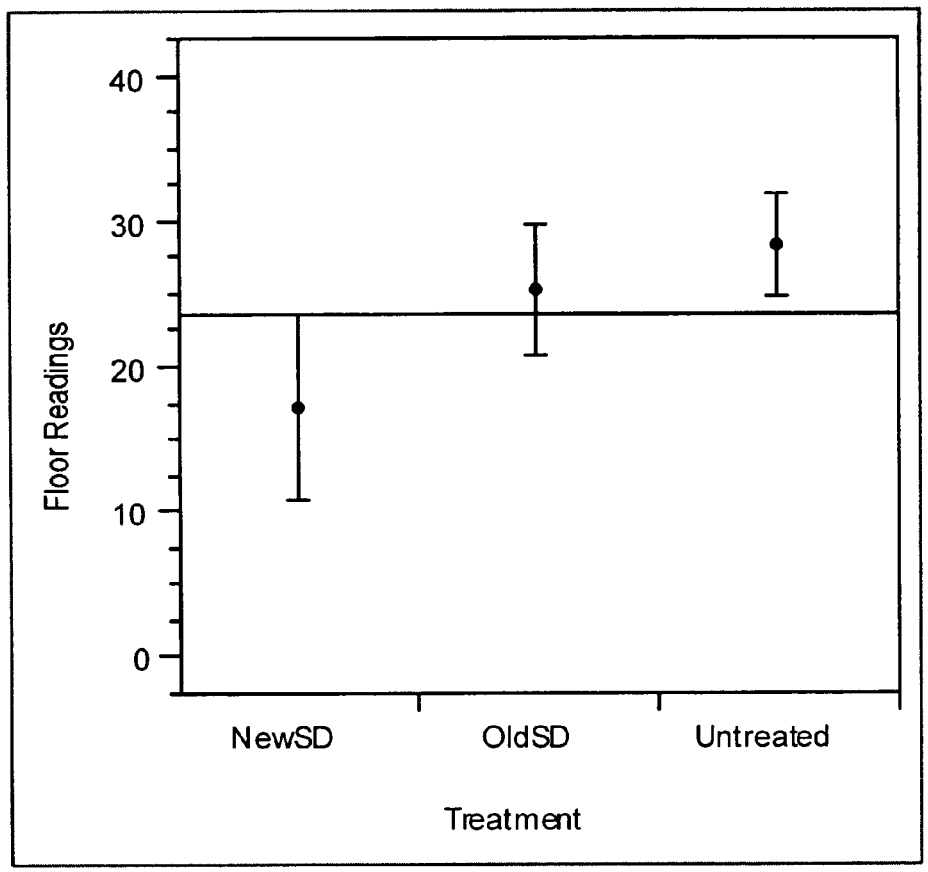
FIG. 6 is a graph of mean (±SE) of ammonia levels (ppm) on urine soaked wooden floors in horse stalls 14 days after treatment with a clay-based particulate material with an antimicrobial agent ("NewSD"), a clay-based particulate material without an antimicrobial agent ("OldSD") and untreated controls after rotation of treatments.

Mean ammonia levels measured over the untreated section were significantly (α<0.001) higher than levels measured over the treated section for each day of the study (see FIG. 1). Expressed as a percentage, the untreated sections had ammonia levels of between 111 percent and 522 percent higher than the treated areas over the course of the study (see FIG. 2).

The permissible ammonia exposure limit (PEL) as published by the AIHA (American Industrial Hygiene Association) is 25 ppm. As can be seen in FIG. 1, the untreated sections had reached this threshold by day 11, whereas the treated sections remained well below the limit at the conclusion of the study. Thus, the present invention can be employed to both reduce ammonia levels and increase times between manure cleanings in poultry facilities.

These results are surprising given that the additive was not used as the primary absorbent, but only a minor quantity was used in admixture with a major quantity of conventional sawdust bedding. This is important because during the first 10-14 days after a new flock of chickens is placed in a barn, mortality rates of chicks' increases with higher ammonia levels.

Example 2

Ammonia Emissions from Horse Manure

Six stalls in a cutting-horse operation were numbered and assigned to one of the following treatments:
1. A naturally occurring particulate comprising a mixture of about 50% diatomaceous earth and about 50% montmorrillonite clay (without antimicrobial agent) sold under the trade name Stall Dry™ ("OriginalSD").
2. A naturally occurring binary mineral particulate of about 50% diatomaceous earth and about 50% montmorrillonite clay into which had been incorporated commercially available Bronopol™ to yield a concentration of about 50 ppm ("AntibacSD").
3. No treatment ("Control").

The wood floors of the stalls were stripped of all shavings and treatments were applied in a quantity of 0.32 kg/m². The floor of each stall was then covered with 0.85 m³ of clean pine wood shavings. Ammonia levels were measured using a Passport™ Five Star Personal Alarm at between 3 and 5 locations in each stall, above and below the shavings, each day for the 14-day duration of the study.

At the mid-point of the study (7 days), the stalls were cleaned of shavings. Ammonia measurements were taken with the ammonia meter placed directly on the floors of the stalls. One kilogram of test materials was sprinkled directly onto urine spots on the floors of the stalls and a fresh layer of shavings was placed over the stall floors.

After the initial 14 days of the study, the stalls were again stripped of shavings and the treatments were rotated by one stall in an anti-clockwise manner. Ammonia measurements were continued daily for 7 days and then on a weekly basis for 4 weeks.

The assignment of treatments was as follows. Before rotation, treatment 1 without antimicrobial agent (Original SD) was assigned to stall numbers 3 & 4, treatment 2 with Bronopol™ (AntibacSD) to stall numbers 5 & 6 and treatment 3 (Control) to stall numbers 7 & 8. After rotation, treatment 1 was assigned to stall numbers 3 & 8, treatment 2 to stalls 4 & 5 and treatment 3 to stalls 6 & 7.

All ammonia measurements were statistically analyzed by ANOVA (Analysis of Variance) and Student's t-test methods.

Results

The mean ammonia levels recorded under the wood shaving bedding materials before and after rotation are set out in FIGS. 3 to 6. Table 1 below summarizes results of ammonia measurements at different time intervals.

TABLE 1

Mean (±SE) Ammonia Levels (PPM) Under Wood Shavings Before Treatment Rotation for Treatments 1, 2 and 3.

| Day # | Treatment | Mean (±SE) Ammonia Level | ANOVA Output |
|---|---|---|---|
| 1-14 | 2 (Antibac) | 11.4 ± 1.52 | DF 116 |
|  | 1 (Original SD) | 19.7 ± 3.02 | F Ratio 5.886 |
|  | 3 (Control) | 25.4 ± 3.91 | Prob > F 0.0037 |

The additive reduced ammonia levels measured below the shavings by an average of approximately 53.1 percent over the 14 days of the study.

Table 2 below summarizes the results of ammonia measurements before rotation of treatment.

TABLE 2

Mean (±SE) Ammonia Levels (PPM) Measured Under Wood Shavings During the First Two Weeks in the Initial Stall before Treatment Rotation for Treatments 1, 2 and 3.

| Day # | Treatment | Mean (±SE) Ammonia Level | ANOVA Output |
|---|---|---|---|
| Period 1-14 | 2 (Antibac SD) | 16.4 ± 2.66 | DF 120 |
|  | 1 (Original SD) | 22.7 ± 2.28 | F Ratio 4.737 |
|  | 3 (Control) | 28.4 ± 3.25 | Prob > F 0.0105 |
| Day 2 | 2 (Antibac SD) | 27.3 ± 8.61 | DF 17 |
|  | 1 (Original SD) | 28.7 ± 6.84 | F Ratio 1.295 |
|  | 3 (Control) | 44.2 ± 9.04 | Prob > F 0.3027 |
| Day 14 | 2 (Antibac SD) | 17.3 ± 6.49 | DF 17 |
|  | 1 (Original SD) | 25.3 ± 4.59 | F Ratio 1.272 |
|  | 3 (Control) | 28.3 ± 3.62 | Prob > F 0.3089 |

For pooled data of ammonia measurements taken from under the treatment areas over the entire duration of the trial, significantly lower levels of ammonia were recorded in stalls treated with AntibacSD compared to stalls treated with shavings alone. An average reduction of 42 percent in ammonia levels was achieved. Further results are listed in FIGS. 3-6 below The results of the study show that the use of the clay-based particulate comprising Bronopol™ bactericide reduced the hydrolysis of ammonia on wood floors of horse stables. Ammonia reduction in stalls treated with the additive was as much as 66 percent lower than levels in untreated stalls. Since the use of the same clay-based particulate without microbial agent produced only slight reductions in ammonia relative to untreated stalls, the ammonia reduction observed in stalls treated with the additive was due to the inhibition of microorganisms responsible for urease production.

As in Example 1, these results are surprising given that the additive was not used as the principal absorbent, but was used in minor quantities in combination with a conventional wood shavings absorbent bedding material.

Ammonia control action can be improved by either increasing the concentration of the antibacterial compound or by adding other materials having ammonia control activity including phosphoric acid, citric acid, acetic acid, aluminum sulphate and urease inhibitors including cyclohexylphosphoric triamide, phenylphosphorodiamidate and n- (n-butyl) thiophosphorictriamide The embodiments of the invention in which an exclusive property or privilege is claimed are defined as follows:
1. A method of reducing ammonia levels in large animal stalls or poultry barns comprising the steps of applying a minor amount of a clay-based particulate material comprising a antimicrobial agent in combination with a major amount of an absorbent bedding material over the floor of said stall or barn, wherein said minor amount of the clay-based particulate material comprising the antimicrobial agent is applied to the floor of said stall or barn and the major amount of said absorbent bedding material is applied over said clay-based particulate.

2. The method according to claim 1 wherein said antimicrobial agent is 1,3-Propanediol, 2-bromo, 2-nitro (Bronopol™).

3. The method according to claim 2 wherein said antimicrobial agent is present in said clay based particulate at a concentration in the range of from 50 to 250 ppm.

4. The method according to claim 2 wherein said clay-based particulate comprises montmorillonite.

5. The method according to claim 2 wherein said clay-based particulate comprises mixture of montmorillonite and diatomaceous earth.

6. The method according to claim 2 wherein said clay-based particulate material is applied at a rate of from 0.22 kg/m$^2$ to 0.43 kg/m$^2$.

7. The method according to claim 2 wherein the average particle size of said clay-based particulate is approximately −24 mesh.

8. The method according to claim 2 wherein the absorbent bedding material is selected from the group comprising straw, saw dust and wood shavings.

9. A method of reducing ammonia levels in large animal stalls or poultry barns comprising the steps of applying a minor amount of a clay-based particulate material comprising a antimicrobial agent in combination with a major amount of an absorbent bedding material over the floor of said stall or barn, wherein said major amount of said absorbent bedding material is applied over the floor of said stall or barn and said minor amount of the clay-based particulate material comprising the antimicrobial agent is applied over said absorbent bedding material.

10. The method according to claim 9 wherein said antimicrobial agent is 1,3-Propanediol, 2-bromo, 2-nitro (Bronopol™).

11. The method according to claim 10 wherein said antimicrobial agent is present in said clay based particulate at a concentration in the range of from 50 to 250 ppm.

12. The method according to claim 10 wherein said clay-based particulate comprises montmorillonite.

13. The method according to claim 10 wherein said clay-based particulate comprises mixture of montmorillonite and diatomaceous earth.

14. The method according to claim 10 wherein said clay-based particulate material is applied at a rate of from 0.22 kg/m$^2$ to 0.43 kg/m$^2$.

15. The method according to claim 10 wherein the average particle size of said clay-based particulate is approximately −24 mesh.

16. The method according to claim 10 wherein the absorbent bedding material is selected from the group comprising straw, saw dust and wood shavings.

17. A method of reducing ammonia levels in large animal stalls or poultry barns comprising the steps of applying a minor amount of a clay-based particulate material comprising a antimicrobial agent in combination with a major amount of an absorbent bedding material over the floor of said stall or barn, wherein said antimicrobial agent is present in said clay-based particulate at a concentration in the range of from 50 to 250 ppm.

18. The method according to claim 17 wherein said antimicrobial agent is 1,3-Propanediol, 2-bromo, 2-nitro (Bronopol™).

19. The method according to claim 17 wherein said clay-based particulate comprises montmorillonite.

20. The method according to claim 17 wherein said clay-based particulate comprises mixture of montmorillonite and diatomaceous earth.

21. The method according to claim 17 wherein said clay-based particulate material is applied at a rate of from 0.22 kg/m$^2$ to 0.43 kg/m$^2$.

22. The method according to claim 17 wherein the average particle size of said clay-based particulate is approximately −24 mesh.

23. The method according to claim 17 wherein the absorbent bedding material is selected from the group comprising straw, saw dust and wood shavings.

24. The method according to claim 17 wherein said minor amount of the clay-based particulate material comprising the antimicrobial agent is admixed with said major amount of said absorbent bedding material before being applied the floor of said stall or barn.

25. A method of reducing ammonia levels in large animal stalls or poultry barns comprising the steps of applying a minor amount of a clay-based particulate material comprising a antimicrobial agent in combination with a major amount of an absorbent bedding material over the floor of said stall or barn, wherein said minor amount of the clay-based particulate material comprising the antimicrobial agent is applied to the floor of said stall or barn at a rate of from 0.22 kg/m$^2$ to 0.43 kg/m$^2$ and the major amount of said absorbent bedding material is applied over said clay-based particulate.

26. The method according to claim 25 wherein said antimicrobial agent is 1,3-Propanediol, 2-bromo, 2-nitro (Bronopol™).

27. The method according to claim 26 wherein said antimicrobial agent is present in said clay based particulate at a concentration in the range of from 50 to 250 ppm.

28. The method according to claim 25 wherein said clay-based particulate comprises montmorillonite.

29. The method according to claim 25 wherein said clay-based particulate comprises mixture of montmorillonite and diatomaceous earth.

30. The method according to claim 25 wherein the average particle size of said clay-based particulate is approximately −24 mesh.

31. The method according to claim 25 wherein the absorbent bedding material is selected from the group comprising straw, saw dust and wood shavings.

* * * * *